(12) United States Patent
Mullen (10) Patent No.: US 10,299,992 B2
(45) Date of Patent: May 28, 2019

(54) SYSTEM AND METHOD FOR DISPENSING PILLS

(71) Applicant: Stephen J. Mullen, Beverly, MA (US)

(72) Inventor: Stephen J. Mullen, Beverly, MA (US)

(*) Notice: Subject to any disclaimer, the term of this patent is extended or adjusted under 35 U.S.C. 154(b) by 0 days.

(21) Appl. No.: 15/250,727

(22) Filed: Aug. 29, 2016

(65) Prior Publication Data

US 2017/0000692 A1    Jan. 5, 2017

Related U.S. Application Data (63) Continuation-in-part of application No. PCT/US2015/017989, filed on Feb. 27, 2015.

(60) Provisional application No. 61/946,262, filed on Feb. 28, 2014.

(51) Int. Cl.
| | |
|---|---|
| *A61J 7/00* | (2006.01) |
| *G06F 19/00* | (2018.01) |
| *A61J 7/04* | (2006.01) |

(52) U.S. Cl.
CPC .............. *A61J 7/0076* (2013.01); *A61J 7/04* (2013.01); *G06F 19/3462* (2013.01); *A61J 2205/60* (2013.01)

(58) Field of Classification Search
CPC ........ A61J 7/0076; A61J 7/04; A61J 2205/60; G06F 19/3462
USPC ................................................ 700/231–244
See application file for complete search history.

(56) References Cited

U.S. PATENT DOCUMENTS

| | | | | |
|---|---|---|---|---|
| 4,473,884 | A | * | 9/1984 | Behl ..................... A61J 7/0481 221/2 |
| 6,961,285 | B2 | | 11/2005 | Niemiec et al. |
| 8,152,020 | B2 | | 4/2012 | Flowers et al. |
| 8,375,957 | B2 | | 2/2013 | Hon |
| 8,424,517 | B2 | | 4/2013 | Sutherland et al. |
| 8,490,628 | B2 | | 7/2013 | Hon |
| 8,550,069 | B2 | | 10/2013 | Alelov |
| 8,670,865 | B2 | * | 3/2014 | Coe ....................... A61J 7/0481 700/232 |
| 8,879,773 | B2 | | 11/2014 | Merenda |
| 8,935,006 | B2 | | 1/2015 | Vu et al. |
| 9,245,093 | B2 | * | 1/2016 | Shaw .................. G06F 19/3462 |

(Continued)

FOREIGN PATENT DOCUMENTS

| | | |
|---|---|---|
| CN | 203563689 | 4/2014 |
| CN | 203814591 | 9/2014 |

(Continued)

OTHER PUBLICATIONS

International Search Report and Written Opinion dated Jun. 5, 2015 in correspondence PCT Patent Application Serial No. PCT/US15/17989.

(Continued)

*Primary Examiner* — Michael Collins
(74) *Attorney, Agent, or Firm* — Grossman, Tucker, Perreault & Pflegler, PLLC (57) ABSTRACT

A system for dispensing pills using a mobile device. The system comprises an expansion case, a pill container, and a dispensing mechanism. The expansion case defines a mobile device compartment configured to receive the mobile device. The expansion case further includes a communication module configured to receive a dispensing signal from the mobile device. The pill container is configured to hold a plurality of pills. The dispensing mechanism is configured to dispense a predetermined number of pills from the pill container in response to the dispensing signal.

15 Claims, 11 Drawing Sheets

(56) References Cited

U.S. PATENT DOCUMENTS

| | | | |
|---|---|---|---|
| 9,358,499 B2 * | 6/2016 | Akdogan | A61J 7/0076 |
| 9,692,829 B2 * | 6/2017 | Starr | H04L 67/12 |
| 2008/0306740 A1 | 12/2008 | Schuck et al. | |
| 2009/0281657 A1 * | 11/2009 | Gak | A61J 7/0481 700/242 |
| 2011/0077061 A1 | 3/2011 | Danze et al. | |
| 2012/0004764 A1 | 1/2012 | Rahilly et al. | |
| 2012/0006847 A1 * | 1/2012 | Coe | A61J 7/0481 222/52 |
| 2012/0035760 A1 | 2/2012 | Portney | |
| 2012/0160716 A1 | 6/2012 | Chan et al. | |
| 2012/0319487 A1 | 12/2012 | Shah | |
| 2013/0247910 A1 | 9/2013 | Postma | |

FOREIGN PATENT DOCUMENTS

| | | |
|---|---|---|
| CN | 104188112 | 12/2014 |
| WO | 2013174002 | 11/2013 |
| WO | 2014017794 | 1/2014 |
| WO | 2014125483 | 8/2014 |
| WO | 2014195805 | 12/2014 |

OTHER PUBLICATIONS

"Compare Automatic Pill Dispensers"; website address: https://www.epill.com/getmedsmart.html; printed on May 17, 2018; 4 pages; e-pill, LLC.

"Automated Medication Dispensing Service"; website address: https://www.lifeline.philips.com/pill-dispenser/health-mdp.html; printed on May 17, 2018; 10 pages; Koninklijke Philips N.V.

"Memo Box Smart Pillbox: Simple Yet Smart Pill Organizer & Reminder"; website address: https://pillbox.tinylogics.com; printed on May 17, 2018; 7 pages; Tinylogics.

"Pill Dispenser—MedMinder—Help your Mom/Dad stay Independent"; website address: https://www.medminder.com; printed on May 17, 2018; 6 pages; MedMinder.

* cited by examiner

SYSTEM AND METHOD FOR DISPENSING PILLS

CROSS REFERENCE TO RELATED APPLICATIONS

This application is a continuation of International Patent Application No. PCT/US15/17989, filed Feb. 27, 2015, designating the U.S. and claiming the benefit of U.S. Provisional Patent Application Serial No. 61/946,262, filed Feb. 28, 2014, the entire disclosures of which are incorporated herein by reference.

FIELD

The present disclosure relates generally to a medication dispensing system and, more particularly, to a mobile device for dispensing pills or medication using an application on a mobile device.

BACKGROUND

Healthcare professionals experience challenges with ensuring patient adherence to medication regimens Improving the quality of the provider/patient relationship is a key component to overcoming these challenges. Some non-adherence solutions help to remind patients of taking their medication according to the regimen. Patients may simply forget to take their medication because they do not have the medication with them when that time arrives. Other solutions request patient reporting of the quantity of medication consumed and the timing of such consumption. Nonetheless, the quality of information is highly dependent on ease of compliance, patient integrity and actual compliance.

Pharmaceutical and healthcare professionals experience challenges with preventing the use of counterfeit drugs. Patients may resort to the use of counterfeit drugs for many reasons, including cost savings, lack of prescription, addiction, etc. Anti-counterfeiting solutions utilize security measures including authentication, specialized package printing and others to curb tampering and diversion of pharmaceutical drugs. Existing measures may control distribution of authentic prescription medication, but some may circumvent the control mechanisms by refilling prescription bottles without authorization or a license to so. However, these measures fail to address the use of counterfeit or unauthorized drugs dispensed from a mobile device and compliance with a medication regimen.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

By way of a general overview, one or more embodiments of the present disclosure may feature a pill dispensing system comprising an expansion case configured to be coupled to a mobile device such as, but not limited to, a smartphone or the like. The expansion case may include a communication module configured to receive a dispensing signal from a dispensing application executing on the mobile device. The dispensing signal may be configured to cause a dispensing mechanism of the expansion case to dispense a predetermined number of pills from one or more pill containers coupled to the expansion case. As described herein, one or more embodiments of the pill dispensing system may address the problems associated with medical non-compliance (e.g., people not taking their pills as directed) and/or counterfeit pills.

Figure 1:
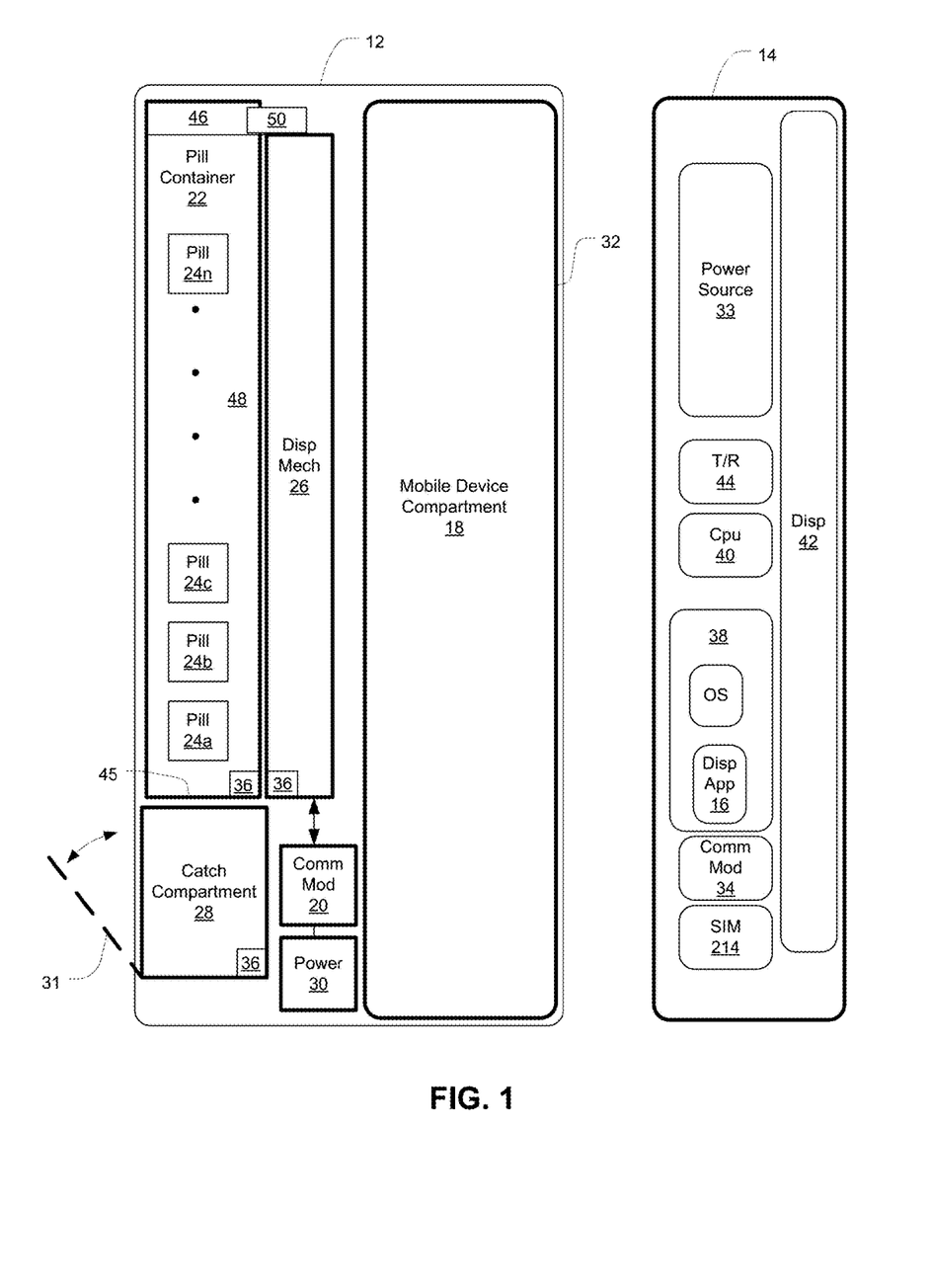
FIG. 1 generally illustrates a pill dispensing system including an expansion case and a mobile device consistent with at least one embodiment of the present disclosure.

Turning now to FIG. 1, one embodiment of a pill dispensing system 10 is generally illustrated. As explained herein, the pill dispensing system 10 may include an expansion case 12 and a mobile device 14 configured to execute one or more pill dispensing applications 16. The mobile device 14 may include any mobile device known to those skilled in the art. For example, the mobile device 14 may include, but is not limited to, a cellular telephone (e.g., smart phone), tablet, Personal Digital Assistant (PDA), notebook computers, netbook, tablet, or the like.

The expansion case 12 may define a mobile device cavity 18 configured to be removably coupled to the mobile device 14, and may also include a communication module 20 for communicating with the mobile device 14, at least one pill container 22 configured to hold a plurality of pills 24a-n, and one or more dispensing mechanisms 26, under control of the pill application 16, configured to dispense a predetermined number of pills 24 into one or more catch compartments 28.

Optionally, the expansion case 12 may include one or more power sources 30 (such as, but not limited to, one or more rechargeable batteries or the like) configured to supply power to the expansion case 12 (e.g., but not limited to, the communication module 20 and/or dispensing mechanism 26). The power source 30 may also optionally provide power to the mobile device 14, for example, to act as a battery backup and/or recharge a primary power source 33 (such as, but not limited to, one or more rechargeable batteries or the like) of the mobile device 14. Alternatively (or in addition), the primary power source 33 of the mobile device 14 may be configured to supply power to the expansion case 12.

The mobile device cavity 18 may be configured to couple the expansion device 12 to the mobile device 14 in any manner known to those skilled in the art. For example, the mobile device cavity 18 may include one or more resiliently deformable sidewalls 32 that are configured to stretch over a least a portion of the mobile device 14 and retain at least a portion of the mobile device 14 within the cavity 18. Optionally, the expansion case 12 (e.g., but not limited to, the mobile device cavity 18) may include one or more fasteners (e.g., but not limited to, mechanical and/or electromagnet fasteners) configured to secure the mobile device 14 at least partially within the mobile device cavity 18. The expansion case 12 may function as a shock absorber to reduce the likelihood of accidental damage to the mobile device 14.

The communication module 20 of the expansion case 12 may be configured to communicate with a communication module 34 of the mobile device 14 using one or more communication protocols. Communication modules 20, 34 are generally configured to enable communication between expansion case 12 and mobile device 14 (e.g., receive and/or transmit data, commands, or other communications), either directly or indirectly. In this regard, communication modules 20, 34 may be configured to enable communication using one or more predetermined wired or wireless communications protocols, such as but not limited to an Internet Protocol, WI-FI protocol, BLUETOOTH protocol, combinations thereof, and the like. Communication modules 20, 34 may therefore include hardware (i.e., circuitry such as, but not limited to, one or more processors, ports, etc.), software, or a combination of hardware and software that allows expansion device 12 to send and/or receive data signals to/from mobile device 14. Communication modules 20, 34 may therefore include one or more transponders, antennas, BLUETOOTH® chips, personal area network chips, near field communication chips, Wi-Fi chips, cellular antennas, USB connection (such as, but not limited to, standard USB, mini USB, micro USB, or the like), Thunderbolt connection, Peripheral Component Interconnect (PCI), Peripheral Component Interconnect Express (PCIe), wired and/or wireless network interface circuitry, combinations thereof, and the like.

The communication module 20 may receive one or more commands from the dispensing application 16, for example, by way of the communication module 34. The communication module 20 of the expansion case 12 may be configured to receive the signal, identify the pill container/pill 22, 24 to be dispensed (e.g., in an embodiment where the expansion case 12 includes a plurality of pill containers 22), optionally identify the number of pills 24 to be dispensed, and to cause the dispensing mechanism 26 to dispense a predetermined number of pills 24 from the selected pill container 22 (e.g., one pill, two pills, etc.). It should be appreciated that while the communication module 20 is shown separately from the dispensing mechanism 26, all or part of the functionality of the communication module 20 may be included in the dispensing mechanism 26.

The communication module 20 may also be configured to transmit information to the dispensing application 16. For example, the communication module 20 may receive a signal from one or more optional sensors 36 (such as, but not limited to, proximity sensors or the like) representative of the intended pill 24 being dispensed into and/or removed from the catch compartment 28. The dispensing application 16 may receive this information, and may use this information to ensure medical compliance as discussed herein. The sensors 36 may also optionally be used to determine the number of pills 24 remaining in a pill container 22. For example, the dispensing application 16 may use this information to determine when to automatically reorder/refill the pill containers 22 and/or notify the user to reorder/refill the pill containers 22 as described herein.

The dispensing application 16 may be stored in one or more one computer-readable storage medium 38 (e.g., memory) having instructions stored thereon which when executed by one or more processor 40 of the mobile device 14, is configured to perform the operations described herein. As discussed herein, the dispensing application 16 may be configured to cause one or more signals to be sent to the communication module 20 and ultimately to cause the dispensing mechanism 26 to dispense a predetermined number of pills 24 from the pill container 22. The dispensing application 16 may include a pill database including corresponding to each pill container 22 and/or type of pill 24 loaded in the expansion case 12. For example, the pill database associated with the dispensing application 16 may include pill information. Pill information may include, but is not limited to, information related to dosage schedule (e.g., but not limited to, how often the user should take the pills 24), dosage amount (e.g., but not limited to, how many pills 24 the user should take each time, and how many pills 24 the user should take overall), dosage instructions (e.g., but not limited to, take with food, do not eat or drink, do not drive after taking, etc.), potential side effects of the pills 24, cross-usage avoidance of the pills 24, and the like.

The pill database may be populated manually and/or automatically. For example, a user could manually enter all or part of the pill information into the pill database associated with the dispensing application 16 using one or more input devices such as, but not limited to, a touch screen display 42, keyboard, camera, scanner/reader, or the like. Alternatively (or in addition), all or part of the pill information may be obtained by loading/downloading a file, for example, from a website, remote server, or the like and/or using the communication module 34 and/or the mobile device transceiver module 44. The user may also identify which pill container 22 (if there is a plurality of pill containers 22 loaded in the expansion case 12) that the pill database corresponds.

Figure 2:
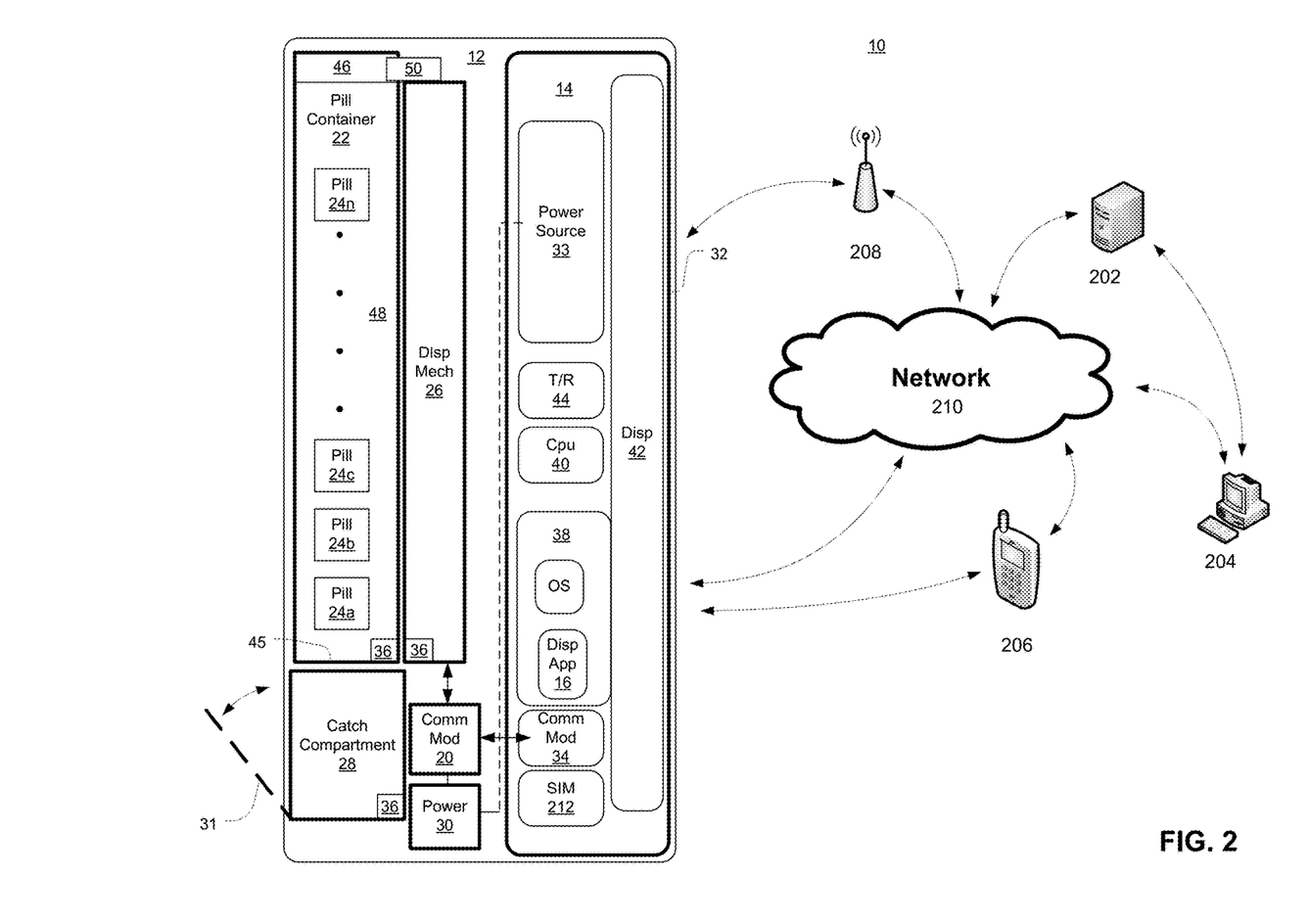
FIG. 2 generally illustrates the pill dispensing system of FIG. 1 communicatively coupled to various devices consistent with at least one embodiment of the present disclosure.

With reference to FIG. 2, the transceiver module 44 is generally configured to enable communication between the mobile device 14 and one or more servers 202, computers, 204, and/or other mobile devices 206, either directly or indirectly (e.g., via access point 208 and/or network 210). In this regard, transceiver module 44 may be configured to enable communication using one or more predetermined wired or wireless communications protocols, such as but not limited to an Internet Protocol, WI-FI protocol, BLUETOOTH protocol, combinations thereof, and the like. Transceiver module 44 may therefore include hardware (i.e., circuitry), software, or a combination of hardware and software that allows mobile device 14 to send and receive data signals to/from other devices. Transceiver module 44 may therefore include one or more transponders, antennas, BLUETOOTH® chips, personal area network chips, near field communication chips, Wi-Fi chips, cellular antennas, combinations thereof, and the like. It should be appreciated that while the transceiver module 44 is shown separately from the communication module 34, all or part of the functionality of the communication module 34 may be included in the transceiver module 44.

The pill database may be at least partially populated using the communication module 34 and/or the mobile device transceiver module 44 of the mobile device 14. For example, while not exhaustive, the user may enter a code, pin, identification number, etc. from a prescription associated with a pill 24 that may automatically populate at least a portion of the pill database with respect to that pill 24 by downloading the pill information from the remote server 202 and/or computer 204. Alternatively (or in addition), the user may set up an account with a remote server/website/computer 202, 204. Upon logging into the account (for example using a username, password, International Mobile Station Equipment Identity (IMEI), subscriber identity module (SIM) 212, or the like), the user may select the pill 24 that is loaded into the expansion case, and the dispensing application 16 may be configured to cause the pill information to be downloaded into the pill database.

In practice, the dispensing application 16 may generate an alert and/or notification to indicate that the user should take one or more pills 24 based, at least in part, on the pill database. The alert/notification include a visual alert/notification shown on the display 42 and/or a visual indicator (e.g., a light emitting diode (LED) light or the like), an auditory alert and/or notification, a vibration alert and/or notification. For example, the dispensing application 16 may generate a visual alert/notification on the display 42. The visual alert/notification may display any pill information stored in the database related to pill 24 such as, but not limited to, what pill 24 the user should take (e.g., if there is more than one type of pill 24 in the pill containers 22), when the user should take the pill 24 (e.g., a time range and/or reminder), how many pills 24 of each type the user should take, any pill administration information (e.g., take with food, do not operate heavy machinery, do not take other medicines, etc.), potential side effects of the pills 24, cross-avoidance of the pills 24 and/or the like.

The dispensing application 16 may receive an acknowledgement from the user that the user intends to take the pill 24. The acknowledgement may include, but is not limited to, the user activating a button/window on the touch screen display 42. Upon receipt of the acknowledgment, the dispensing application 16 may cause a dispensing signal to be transmitted to the communication module 20 of the expansion case 12. The dispensing signal may include information indicating/representative of which type of pill 24 to be dispensed and/or which pill container 22 to dispense from, and/or how many pills 24 to dispense. The communication module 20 may then cause the dispensing mechanism 26 to dispense the appropriate pill 24 from the selected pill container 22. The pill(s) 24 may then drop into the catch compartment 28. Thereafter, the user may remove the pill(s) 24 from the catch compartment 28, for example, by opening a door 31 or the like.

Optionally, one or more sensors 36 may generate a signal indicating/representative of the pills 24 having been removed from the catch compartment 28. For example, one or more of the sensors 36 may include a proximity sensor or the like disposed in the pill container 22, the catch compartment 28, and/or the dispensing mechanism 26 which represents that a pill 24 has been removed from the pill container 22 and/or the catch compartment 28. Alternatively (or in addition), one or more sensors 36 may include a switch or the like that generates a signal which represents that the door 31 of the catch compartment 28 has been opened after the pill 24 was dispensed form the pill container 22. It should be appreciated that one or more of the catch compartments 28 may be integral and/or unitary with the expansion case 12, pill container 22, and/or dispensing mechanism 26.

The dispensing application 16 may keep track of when the user has taken the pill(s) 24. For example, the dispensing application 16 may receive a medical compliance signal transmitted by the communication module 20, e.g., based on the signal(s) from the sensors 36. Alternatively (or in addition), the dispensing application 16 may keep track of whether the user acknowledges to dispense the pill(s) 24. The dispensing application 16 may determine the next dosage based (at least in part) on the medical compliance signal, pill dispensing acknowledgement, and/or other pill information contained in the pill database. For example, the dispensing application 16 may recalculate the next dosage time and/or quantity based on whether and/or when the user took the pills (24).

Optionally, the dispensing application 16 may generate a compliance alert to indicate that the user has taken the pill(s) 24. For example, the dispensing application 16 may be configured to cause the compliance alert to be transmitted to one or more predetermined entities (such as, but not limited to, the user's doctor, pharmacy, remote computer/server, and/or other specified individuals), for example, using the transceiver module 44 as described herein. The compliance alert/notification may be useful in diagnosing and/or treating a patient/user, and to ensure that the patient/user is taking their pills 24 at the appropriate times (e.g., ensuring medical compliance). Additionally, the compliance alert/notification may be useful in diagnosis potential side effects of the pills 24.

The dispensing application 16 may also keep track of how many pills 24 are remaining in the pill container 22 and/or when the quantity of pills 24 fails below a threshold amount. For example, the dispensing application 16 may be aware of how many pills 24 are originally contained in the pill container 22, and may count down as the pills 24 are dispensed. Alternatively (or in addition), the pill container 22 and/or dispensing mechanism 26 may include one or more sensors 36 that determine how many pills are remaining in the pill container 22 and/or when the quantity of pills 24 in the pill container 22 fails below a threshold amount. Based on the pill tracking information, the dispensing application 16 may generate a notification to remind the user to reload the pill container 22 and/or may automatically order additional pill containers 22 and/or pills 24, for example, using the transceiver module 44 as described herein.

The dispensing application 16 may also generate a non-compliance alert/notification in the event that that the user does not take the pill(s) 24 within the determined time range. For example, the dispensing application 16 may be configured to generate a non-compliance alert/notification if the user does not enter an acknowledgement to the pill dispensing notification and/or the does not receive a medical compliance signal from the expansion case 12. According to one embodiment, the dispensing application 16 may be configured to cause the non-compliance alert to be transmitted to one or more predetermined entities (such as, but not limited to, the user's doctor, pharmacy, remote computer/server, and/or other specified individuals), for example, using the transceiver module 44 as described herein. The non-compliance alert/notification may be useful in detecting medical non-compliance, diagnosing and/or treating a patient/user, and to ensure that the patient/user is taking their pills 24 at the appropriate times. For example upon receipt of a non-compliance alert, appropriate action may be taken to remind and/or ensure that the user/patient takes the pills 24 at the appropriate times. Additionally, the non-compliance alert/notification may be useful in diagnosis potential side effects of the pills 24.

The dispensing application 16 may also be aware of which pills 24 are remaining in the pill containers 22. For example, one or more of the pill containers 22 may be loaded with two or more different types of pills 24. The dispensing application 16 may be aware of which types of pills 24 are loaded in a particular pill container 22, and the order of the pills 24 within the pill container 22. As such, the dispensing application 16 may be configured to dispense different types of pills 24 from the same pill container 22 based on the appropriate dosing schedule. In the event that a user does not take a particular pill 24 at the appropriate time, the dispensing application 16 may be configured to generate a warning to inform the user to disregard one or more pills 24 until the appropriate pill 24 is dispensed based on the dosing schedule. As such, the number of pill containers 22 necessary to dispense user's pills for a given time frame may be reduced.

As discussed herein, the expansion case 12 may include one or more pill containers 22. Each pill container 22 may be configured to hold one or more (e.g., a plurality) of pills 24a-n. For example, the pill container 22 may include one or more pill cavities 48 configured to hold one or more pills 24a0-n. The pills 24a-n may include any type of pill known to those skilled in the art such as, but not limited to, tablets, capsules, and variants thereof like caplets. The pills 24a-n may include prescription pills, over-the-counter pills, vitamins, supplements, and the like. The pills 24a-n may have any shape.

One or more pill containers 22 may be integral and/or unitary with the expansion case 12. For example, the pill containers 22 may optionally include one or more lids, covers, or the like 46 configured to allow pills 24 to be loaded into one or more pill cavities 48 of the pill container 22. The pill container 22 may also optionally include one or more pill discharge aperture 45 configured to allow a selected pill 24 dispensed from the pill container 22/pill cavity 48 to exit the pill container 22 (e.g., to exit the pill container 22 and fall into the catch compartment 28).

Figure 3:
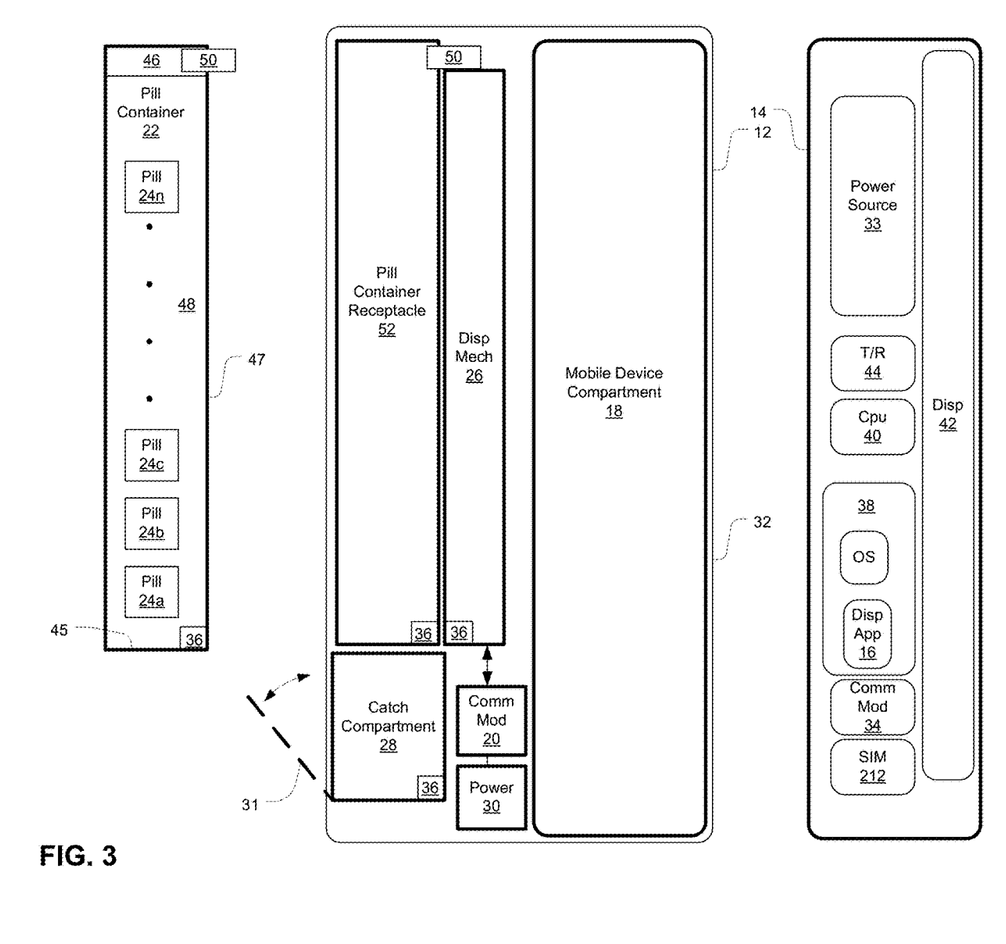
FIG. 3 generally illustrates an exploded view of a pill dispensing system consistent with FIG. 1.

Alternatively (or in addition), one or more pill containers 22, FIG. 3, may be configured to be removably coupled to the pill dispensing system 10. According to one embodiment, a pill container 22 may be configured to be removably coupled to the expansion case 12 and/or dispensing mechanism 26. For example, a pill container 22 may include a pill container body/housing 47 configured to hold one or more pills 24a-n. According to one embodiment, the pill container body/housing 47 may define one or more pill cavities 48 and (optionally) one or more pill discharge aperture 45 as described herein. The pill container body/housing 47 may be configured to be removably secured to the expansion case 12 and/or dispensing mechanism 26.

According to one embodiment, the expansion case 12 may optionally include one or more pill container receptacles/cavities 52 configured to be removably coupled to one or more pill containers 22 (e.g. the pill container body/housing 47). For example, the pill container 22 and/or the expansion case 12 (e.g., the pill container body/housing 47) may include one or more fasteners 50 configured to removably secure the pill container 22 to the expansion case 12. The fastener(s) 50 may include any type of fastening devices known to those skilled in the art such as, but not limited to, clips, mounts, biased tabs, grooves, slots, recesses, clamps, or the like.

As discussed herein, the user may identify which pill container receptacle/cavity 52 that the pills 24 in a specific pill container 22 are secured so that the dispensing application 16 (and/or the communication module 20 and/or dispensing mechanism 26) may determine which pill 24 to dispense from which pill container 22. According to one embodiment, the expansion case 12 may include a plurality of pill container receptacles 52, wherein each pill container receptacle/cavity 52 corresponds to a unique pill container 22 configuration (e.g., but not limited to, size, shape, and/or fastener 50). One or more of the pill container receptacles 52 may be configured to be coupled to different pill container configurations (e.g., but not limited to, size, shape, and/or fastener 50).

The pill containers 22 may be loaded with pills 24a-n by the user and/or a third party. According to one embodiment, the pill containers 22 may be loaded with pills 24a-n by a doctor, a pharmacy, a distributor, and/or a manufacturer. The pill containers 22 may optionally include tamper resistant and/or proof. For example, in an embodiment where the pill container 22 is filled with pills 24a-n by a doctor, a pharmacy, a distributor, and/or a manufacturer, the pill container 22 may be tamper resistant to ensure that the pills are authentic (e.g., not counterfeit) and have not be modified or altered with since having been loaded by the doctor, the pharmacy, the distributor, and/or the manufacturer.

While the pill containers 22 are generally illustrated having an elongated, generally tubular and/or rectangular configuration, it should be appreciated that the pill containers 22 may have any size and/or shape.

Figure 4:
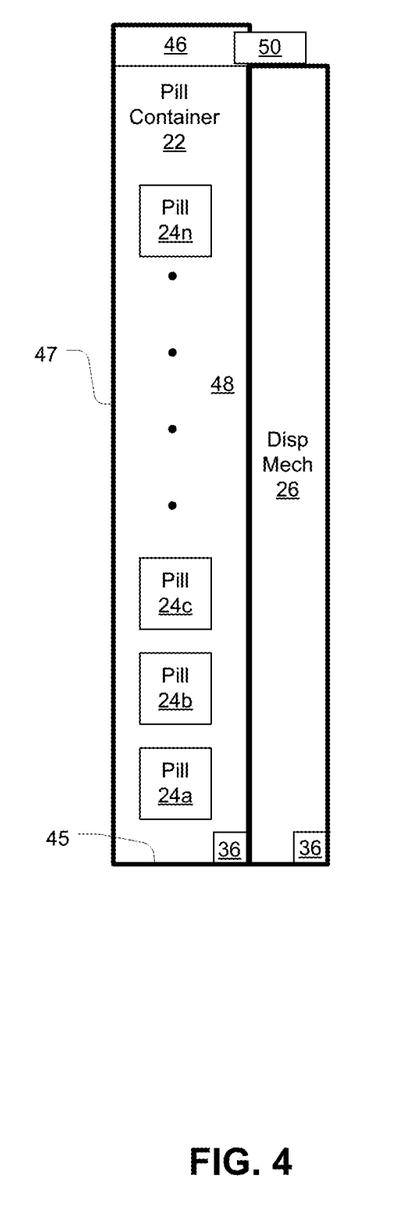
FIG. 4 generally illustrates another embodiment of a pill container and dispensing mechanism consistent with at least one embodiment of the present disclosure.

Referring back to FIG. 1, the expansion case 12 also includes one or more dispensing mechanisms 26. One or more of the dispensing mechanisms 26 may be integral and/or unitary with the expansion case 12. Alternatively (or in addition), one or more of the dispensing mechanisms 26 may be integral and/or unitary with the pill container 22, for example, as generally illustrated in FIG. 4.

The dispensing mechanism 26 may include any dispensing mechanism known to those skilled in the art configured to dispense a predetermined, controlled number of pills 24 from one or more selected pill containers 22. For example, the dispensing mechanism 26 may include one or more solenoids, actuators, springs, doors, flaps, augers, rotary carousels, or the like, configured to allow a predetermined, controlled number of pills 24 to be dispensed from one or more selected pill containers 22.

Figure 5:
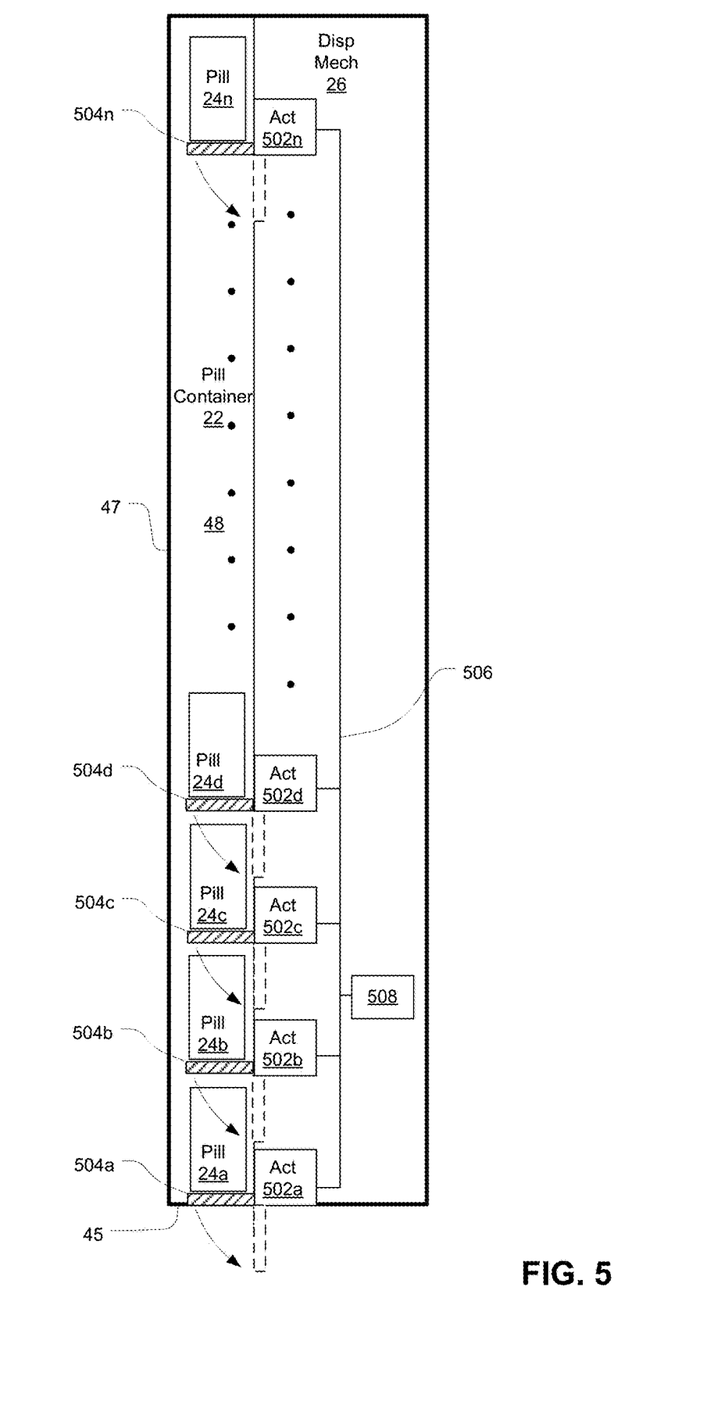
FIG. 5 generally illustrates a further embodiment of a pill container and dispensing mechanism consistent with at least one embodiment of the present disclosure.

One embodiment of a dispensing mechanism 26 is generally illustrated in FIG. 5. The dispensing mechanism 26 may include a plurality of actuators 502a-n. For example, each actuator 502a-n may be configured to cause a corresponding retaining member 504a-n to selectively move from a first position, wherein the retaining member 504 holds a corresponding pill 24 within the pill cavity 48 to a second position (indicated in dashed lines), wherein the corresponding pill 24 may exit the pill cavity 48 and enter into the catch compartment 28 (FIG. 1) whereby the user may take the pill 24. With continued reference to FIG. 5, the dispensing mechanism 26 may include one or more communication buses 506 or the like which may be configured to receive signals to activate a selected actuator 502a-n, for example, by way of a communication port/interface 508 which may receive the signals from the communication module 20 (FIG. 1).

While the dispensing mechanism 26 is shown integral with the pill container 22, it should be appreciated that the dispensing mechanism 26 may be separate from the pill container 22 and/or partially separate from the pill container 22. For example, the retaining members 504a-n may be integral with the pill container 22, while the rest of the dispensing mechanism 26 (e.g., the actuators 502a-n, bus 506, and/or communication portion 508) may be separate from the pill container 22. According to at least one embodiment, at least a portion of the dispensing mechanism 26 (e.g., the actuators 502a-n, bus 506, and/or communication portion 508) may be integral with the expansion case 12.

Figure 6:
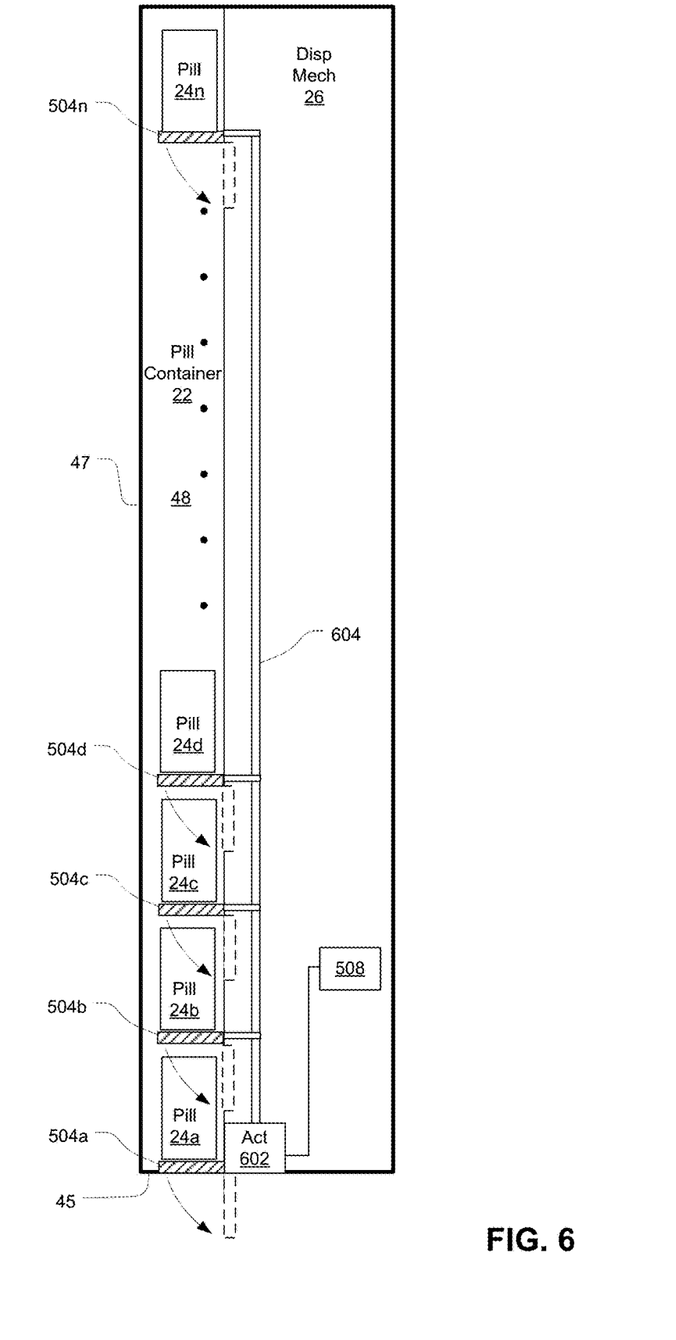
FIG. 6 generally illustrates yet another embodiment of a pill container and dispensing mechanism consistent with at least one embodiment of the present disclosure.

Referring now to FIG. 6, another embodiment of a dispensing mechanism 26 is shown. The dispensing mechanism 26 may include a single actuator 602 configured to cause a plurality of retaining member 504a-n to selectively move. For example, the actuator 602 may be coupled to a cam, lever, or the like 604. The actuator 602 may be configured to move the cam 604 (e.g., to rotate the cam 604 along its longitudinal axis). As the cam 604 rotates into a predetermined position, a selected one of the retaining member 504a-n may move from the retaining position (as shown) to a dispensing position (shown in dotted lines). As such, the dispensing mechanism 26 may be configured to selectively dispense a selected pill 24 from the pill container 22.

Figure 7:
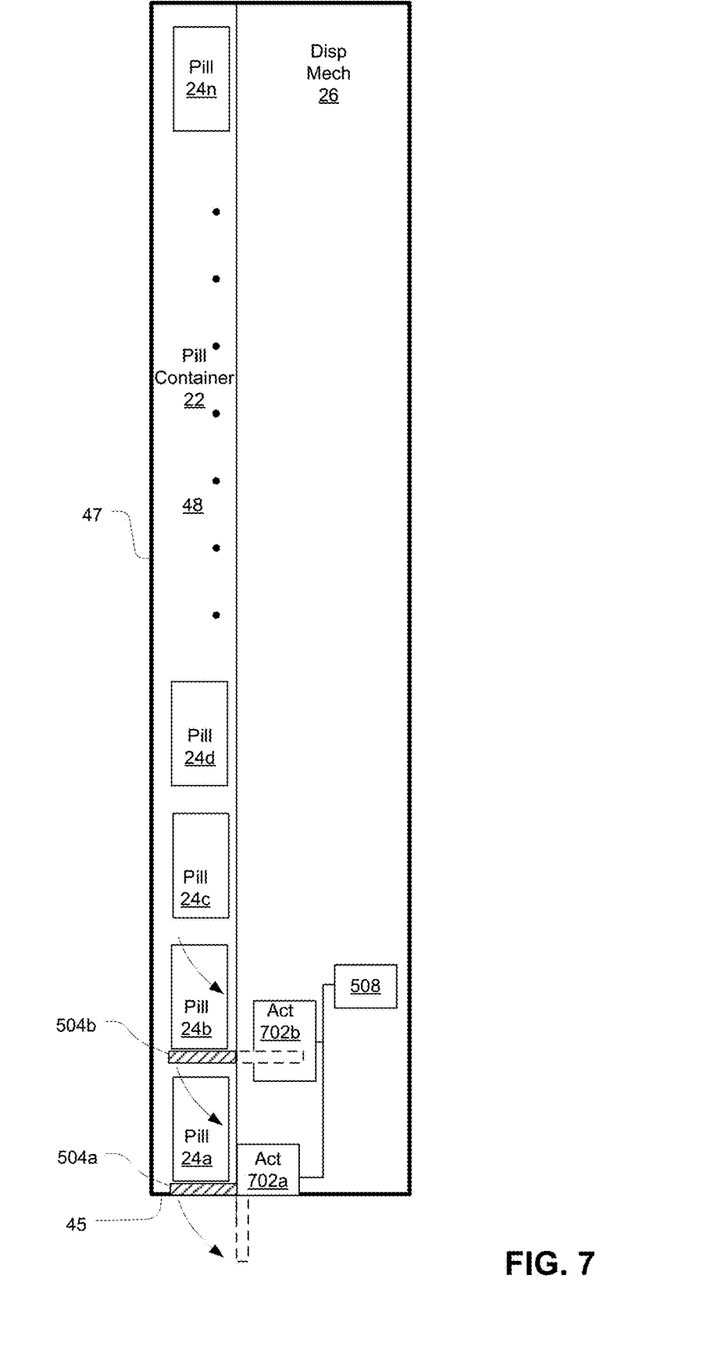
FIG. 7 generally illustrates yet a further embodiment of a pill container and dispensing mechanism consistent with at least one embodiment of the present disclosure.

Turning now to FIG. 7, yet another embodiment of a dispensing mechanism 26 is shown. The dispensing mechanism 26 may include a first actuator 702a configured to cause a first retaining member 704a to selectively move, and a second actuator 702b configured to cause a pinching retaining member 704a to selectively move. For example, the first actuator 702a may be configured to cause the first retaining member 704a to move from the retaining position as shown, to a dispensing position (e.g., as shown in dotted lines), thereby allowing a selected pill(s) 24 to drop into the catch compartment 28 (see, for example FIG. 1). After the selected pill(s) 24 have been dispensed, the first actuator 702a may be configured to cause the first retaining member 704a to move back to the retaining position as shown. Thereafter, the second actuator 702b may be configured to move the pinching retaining member 704a (e.g., as shown in the dotted l lines) to allow the next pill (e.g., pill 24b as shown) to move into the space vacated by the dispensed pill (e.g., pill 24a as shown). As the pill (e.g., pill 24b) adjacent to the dispensed pill (e.g., pill 24a) moves into the vacated space, the second actuator 702b may be configured to move the pinching retaining member 704a back into the retaining position as shown. As such, a new pill (e.g., pill 24b) is ready to be dispensed by the first actuator 702a/first retaining member 704a. While the pinching retaining member 704b is shown extending generally below the pill 24b generally across the cross-section of the pill cavity 48, it may be appreciated that the pinching retaining member 704b may extend only partially across the pill cavity 48 and/or may pitch the pill 24b against a sidewall of the pill cavity 48 to generally retain the pill 24b.

Figure 8:
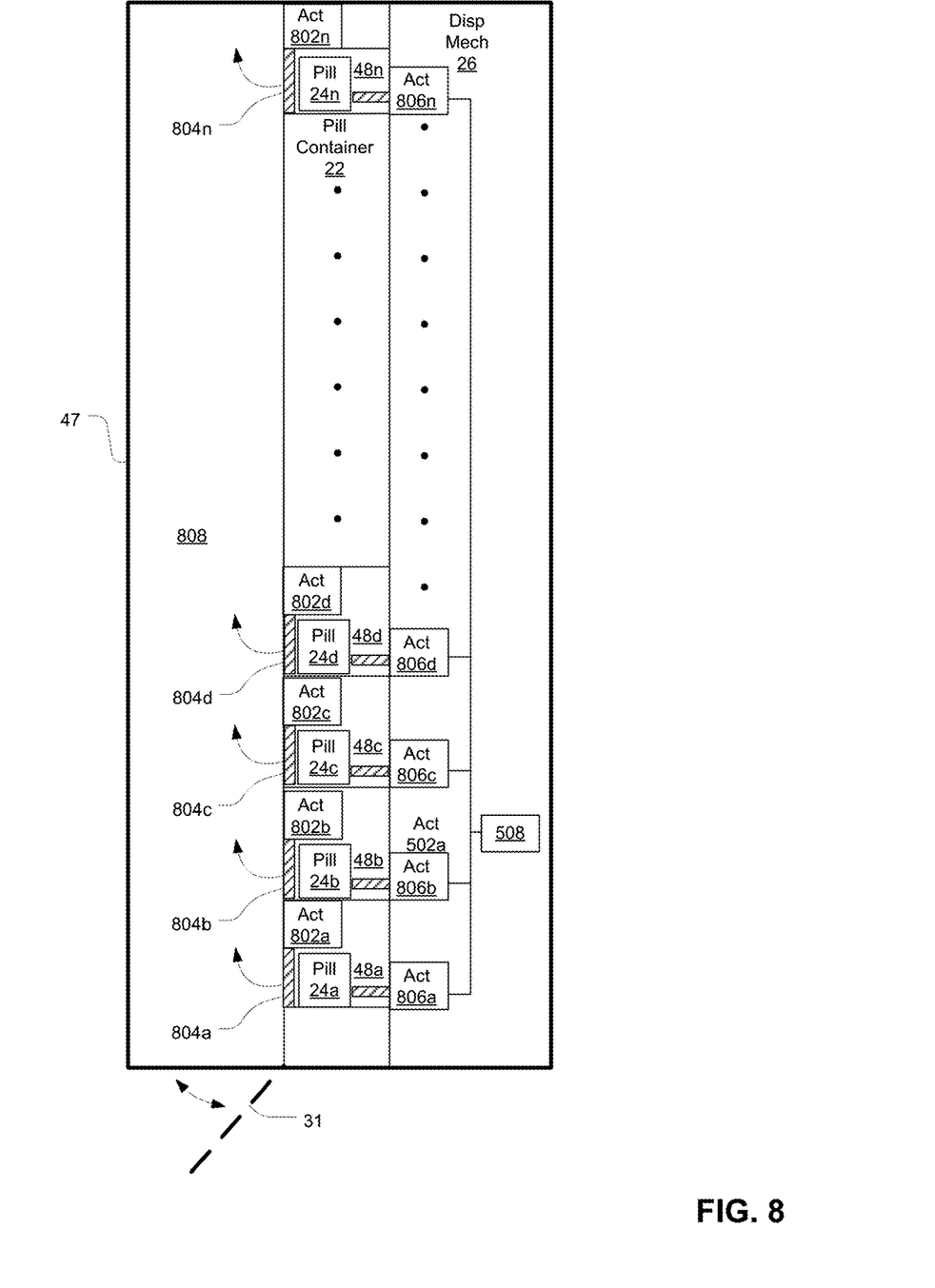
FIG. 8 generally illustrates an additional embodiment of a pill container and dispensing mechanism consistent with at least one embodiment of the present disclosure.

With reference to FIG. 8, a further embodiment of a pill container 22 and a dispensing mechanism 26 is generally illustrated. The pill container 22 may include a plurality of pill cavities 48a-n, each pill cavity 48 configured to hold one or more pills 24 (only one pill 24a-n is shown in each pill cavity 48a-n for simplicity). A first actuator 802a-n may be provided to cause a retaining member 804a-n corresponding to each pill cavity 48a-n to move from a retaining position (e.g., as generally shown) to a dispensing position (e.g., as generally indicated by the arrows) upon which the selected pill(s) 24 in the selected pill cavity 48 may be dispensed. In the illustrated embodiment, each pill cavity 48a-n has a respective one of a plurality of actuators 802a-n, however, it should be appreciated that a plurality of retaining members 804a-n may be opened/closed by one actuator 802. Optionally, one or more pill pushing actuators 806a-n may be provided to urge the selected pill(s) 24 out of the selected pill cavity 48. Once the selected pill(s) 24 are dispensed from the selected cavity 48, the selected pill(s) 24 may fall into one or more dispensing cavities 808. The dispensing cavity(ies) 808 may be separate from or the same as, the catch compartment 28. One or more doors 31 may optionally be provided to remove the selected pill(s) 24 therefrom.

Figure 9:
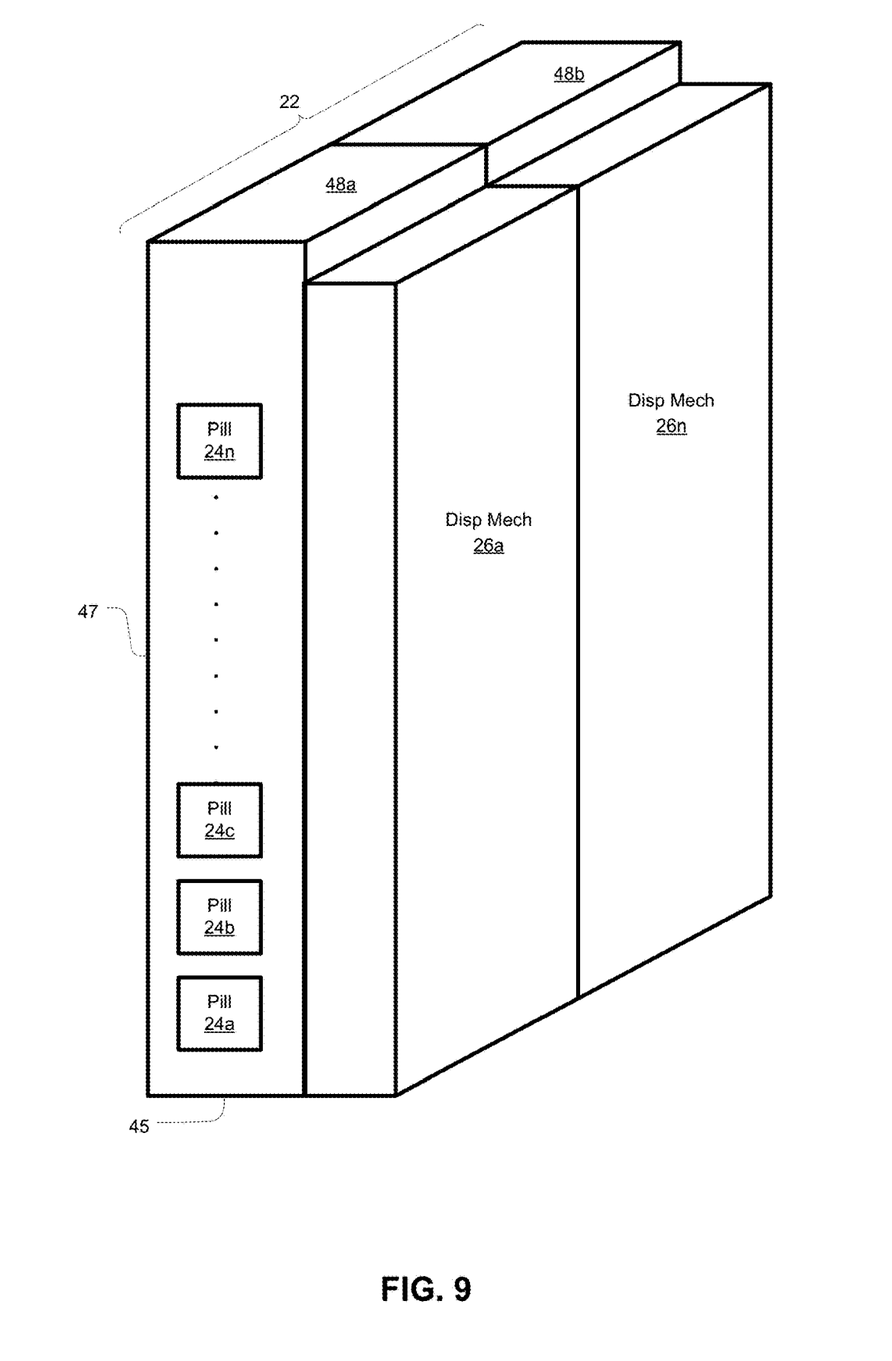
FIG. 9 generally illustrates another further embodiment of a pill container and dispensing mechanism consistent with at least one embodiment of the present disclosure.

Turning now to FIG. 9, yet another embodiment of a pill container 22 is generally shown. The pill container 22 may define a plurality of pill cavities 48a-n. Each pill cavity 48 may be configured to hold one or more pills 24. One or more of the pills 24 in each cavity 48 may be the same and/or different. The pill container 22 and/or the expansion case 12 may optionally include one or more dispensing mechanisms 26a-n as described herein.

Figure 10:
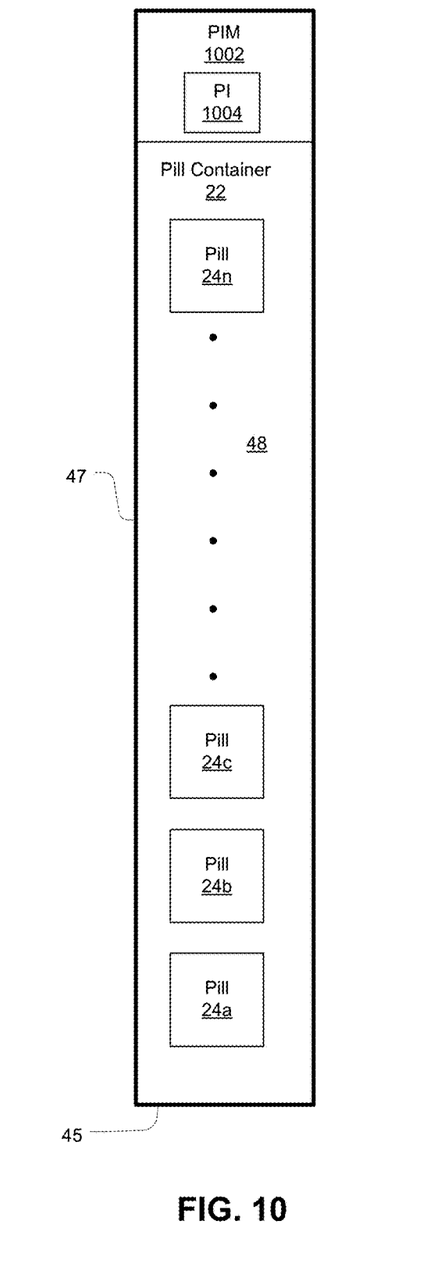
FIG. 10 generally an embodiment of a pill container including a pill identification module consistent with at least one embodiment of the present disclosure.
Figure 11:
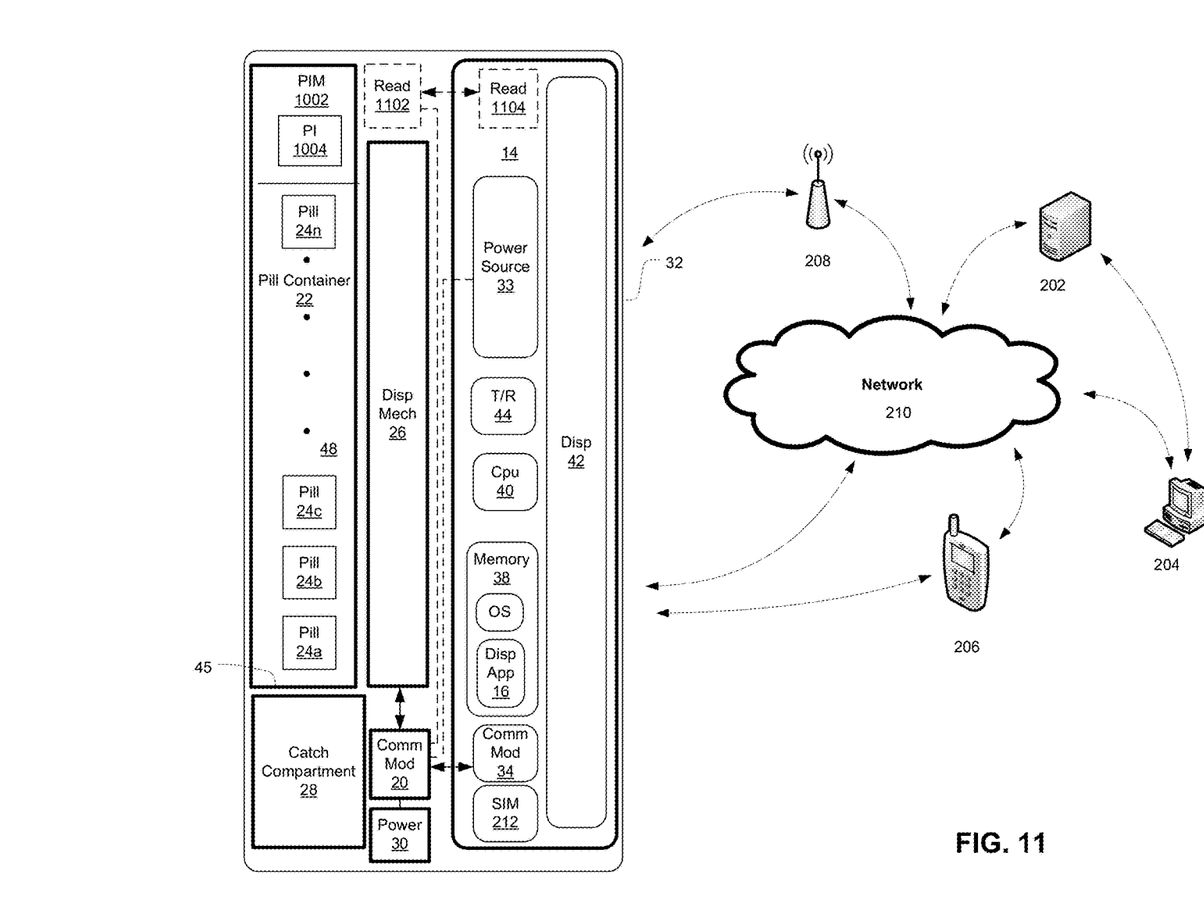
FIG. 11 generally an embodiment of a pill dispensing system including a pill container including a pill identification module consistent with at least one embodiment of the present disclosure.

Turning now FIGS. 10 and 11, a further embodiment of a pill container 22 consistent with the present disclosure is generally illustrated. The pill container 22 may be similar to any pill container described herein, except that the pill container 22 may also include one or more pill identification modules (PIM) 1002. The PIM 1002 may include, but is not limited to, one or more computer readable storage mediums (memories), optical machine-readable codes (e.g., 2D and/or 3D matrix codes (e.g., Response (QR) codes), barcodes, or the like) near field communication chips, radio-frequency identification (RFID) chips, or the like. According to one embodiment, the PIM 1002 may directly store pill information related to the pill(s) 24 stored in the pill container 22 used by the dispensing application 16 (e.g., to populate the pill database) as described herein.

In addition (or alternatively), the PIM 1002 may be configured to include (e.g., stored thereon) at least one pill identification (PI) 1004 associated with the pill(s) 24 contained within the pill cavity 48. The PI 1004 may be provided by a manufacturer of the pills, a distributor of the pills, a pharmacy, a doctor, or the like, and may be used, for example by the dispensing application 16 (FIG. 1), to obtain pill information about the pill(s) 24 contained within the pill container 22 (e.g., as described herein to populate the pill database associated with the dispensing application 16), authenticate the pill(s) 24 and/or the user, automatically reorder pills 24/pill containers 22, and/or keep track of potential pill recalls. For example, the expansion case 12 and/or the mobile device 14 may include one or more portions, interfaces, sensors, readers, or the like 1102, 1104 (FIG. 11) to read (either wirelessly or wired) the PI 1004 from the PIM 1002. The PI 1004 may be used by the dispensing application 16 and/or transmitted to a remote server/computer/website 202, 204, 206 to automatically download pill information related to the pill(s) 24 within the pill container 22 and to populate the pill database.

According to one embodiment, the PI 1004 may be encrypted. For example, the PI 1004 may be encrypted using any known encryption technique such as, but not limited to, a public/private key encryption. Once the pill container 22 is secured to the expansion case 12 as described herein, one or more readers 1102, 1104 may obtain the encrypted PI 1004. The expansion case 12 (e.g., but not limited to, the communication module 20) and/or the mobile device 14 may optionally decrypt the PI 1004. Alternatively (or in addition), the mobile device 12 may transmit the encrypted PI 1004 to remote server/computer/website 202, 204, 206. In either case, the PI 1004 may optionally be used (by either the mobile device 14 and/or the remote server/computer/website 202, 204, 206) to authenticate the pills 24. The dispensing application 16 may be configured to not dispense the pills 24 in the event that the pills 24 cannot be authenticated. As may therefore be appreciated, counterfeiting and/or tampering of the pills 24 may be avoided.

The PIM 1002 may also optionally include information related to the user and/or the user's prescription. For example, the PIM 1002 may include user identification/prescription identification which may be compared with user identification stored on the mobile device 14 and/or remote server/computer/website 202, 204, 206. For example, the user information/prescription identification stored on the PIM 1002 may be compared with a user name and/or password, hardware associated with the (such as, but not limited to, the IMEI, SIM, and/or processor id 212), or the like to authenticate the user and ensure that the prescription belongs to the user. The dispensing application 16 may be configured to not dispense the pills 24 in the event that the user cannot be authenticated. As may therefore be appreciated, authenticating the user may prevent/reduce the likelihood of an unauthorized user dispensing pills 24. The user authentication may be performed when the pill container 22 is secured to the expansion case 12 and/or before dispensing pills 24.

According to one aspect, the present disclosure features a system for dispensing pills using a mobile device. The system comprises an expansion case, a pill container, and a dispensing mechanism. The expansion case defines a mobile device compartment configured to receive the mobile device. The expansion case further includes a communication module configured to receive a dispensing signal from the mobile device. The pill container is configured to hold a plurality of pills. The dispensing mechanism is configured to dispense a predetermined number of pills from the pill container in response to the dispensing signal.

According to another aspect, the present disclosure features system for dispensing pills. The system includes a mobile device, an expansion case, a pill container, and a dispensing mechanism. The mobile device is configured to execute a dispensing application. The dispensing application is configured to generate a dispensing signal based, at least in part, on pill information. The expansion case defines a mobile device compartment configured to receive the mobile device. The expansion case further includes a communication module configured to receive a dispensing signal from the mobile device. The pill container is configured to hold a plurality of pills. The dispensing mechanism is configured to dispense a predetermined number of pills from the pill container in response to the dispensing signal.

According to a further aspect, the present disclosure features a system. The system includes, inter alia, a pill container including a pill container body and a pill identification module (PIM). The pill container body is configured to be removably coupled to a pill dispensing system and is further configured to hold a plurality of pills.

The PIM may include a pill identification (PI) associated with the plurality of pills in the pill container. The PI may optionally be encrypted. The PIM may be used to obtain pill information related to the plurality of pills in the pill container. For example, the PIM may include the pill information stored thereon. Alternatively, or in addition, a dispensing application may obtain the pill information based on the PIM. The pill information may include a dosage schedule.

While the expansion case has been described as being configured to receive a mobile device, it may be appreciated that the functionality of the expansion case and the mobile device may be combined into an integrated and/or unitary pill dispensing system. As may therefore be appreciated, the mobile device compartment 18 may therefore be eliminated, and the functionality of the communication modules 20, 34 and/or the mobile device transceiver module 44 may be partially and/or wholly combined. The unitary pill dispensing system (i.e., a pill dispensing system as described herein) may be either portable or non-portable (e.g., stationary). For example, the unitary pill dispensing system may be powered by one or more power sources (e.g., rechargeable batteries or the like) and/or may be configured to be hard wired to an electrical outlet. The unitary pill dispensing system may also be configured to communicate with other devices (e.g., a local and/or remote server/website/computer) either wireless communication protocol or using a wired communication protocol. The unitary pill dispensing system may also be configured include any of the dispensing mechanisms and/or pill containers described herein (either integral/unitary with the unitary pill dispensing system and/or configured to be removably coupled thereto). For example, while not intended to be limiting, the unitary pill dispensing system may be configured to be removably coupled with a pill container including a PIM as described herein.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

As used in any embodiment herein, the term "module" may refer to software, firmware and/or circuitry configured to perform one or more operations consistent with the present disclosure. Software may be embodied as a software package, code, instructions, instruction sets and/or data recorded on non-transitory computer readable storage mediums. Firmware may be embodied as code, instructions or instruction sets and/or data that are hard-coded (e.g., non-volatile) in memory devices. "Circuitry", as used in any embodiment herein, may comprise, for example, singly or in any combination, hardwired circuitry, programmable circuitry such as computer processors comprising one or more individual instruction processing cores, state machine circuitry, software and/or firmware that stores instructions executed by programmable circuitry. The modules may, collectively or individually, be embodied as circuitry that forms a part of one or more devices, as defined previously.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A system for dispensing pills using a mobile device, the system comprising:
    an expansion case defining a mobile device compartment configured to receive the mobile device, the expansion case further including a communication module configured to receive a dispensing signal from the mobile device;
    a pill container removably coupled to the expansion case, the pill container defining a housing, the housing including:
        at least one pill cavity configured to hold one or more pills; and
        a pill identification module (PIM) configured to store predetermined pill information comprising a dosage schedule, the predetermined pill information being stored prior to the pill container being coupled to the expansion case;
    a dispensing application configured to be executed on the mobile device, wherein the dispensing application is configured to obtain the dosage schedule from the PIM and generate the dispensing signal based on, at least in part, the dosage schedule; and
    a dispensing mechanism configured to dispense a predetermined number of pills from the pill container in response to the dispensing signal.

2. The system of claim 1, wherein the dispensing mechanism is integral with the expansion case.

3. The system of claim 1, wherein the dispensing mechanism is integral with the pill container.

4. The system of claim 1, wherein the PIM includes a pill identification (PI) associated with the one or more pills.

5. The system of claim 4, wherein the PI is encrypted.

6. The system of claim 5, wherein the dispensing application is configured to only generate the dispensing signal if the PI is authenticated.

7. The system of claim 4, wherein the PI is used to obtain pill information related to the one or more pills.

8. The system of claim 1 further comprising a plurality of the pill containers, each pill container configured to hold a different type of pill compared to the other pill containers.

9. The system of claim 8, wherein the communication module is configured to cause the dispensing mechanism to dispense a selected one of the pills from a selected one of the plurality of pill containers.

10. The system of claim 9, further comprising a plurality of pill dispensing mechanisms, each pill dispensing mechanism corresponding to one of the plurality of pill containers.

11. The system of claim 1, wherein the PIM includes at least one memory.

12. The system of claim 1, wherein the PIM includes at least one of an optical machine readable code, a near field communication chip, or a radio-frequency identification (RFID) chip.

13. The system of claim 1, wherein said dispensing application is configured to cause pill information to be obtained based, at least in part, on the PIM.

14. The system of claim 1, wherein the PIM is used to obtain pill information related to the one or more pills.

15. The system of claim 1, wherein the pill container is separate from the mobile device.

* * * * *